US012740885B2

(12) United States Patent
Chen et al.

(10) Patent No.: US 12,740,885 B2
(45) Date of Patent: Sep. 22, 2026

(54) STERNUM STABILIZATION VEST

(71) Applicants: National Taiwan University, Taipei City (TW); National Taiwan University Hospital Hsin-Chu Branch, Hsinchu County (TW)

(72) Inventors: Yih-Sharng Chen, Taipei City (TW); Hsiao-En Tsai, Hsinchu County (TW); Ming-Hsien Lin, Hsinchu County (TW)

(73) Assignees: NATIONAL TAIWAN UNIVERSITY, Taipei City (TW); NATIONAL TAIWAN UNIVERSITY HOSPITAL HSIN-CHU BRANCH, Hsinchu County (TW)

( * ) Notice: Subject to any disclaimer, the term of this patent is extended or adjusted under 35 U.S.C. 154(b) by 0 days.

(21) Appl. No.: 19/035,345

(22) Filed: Jan. 23, 2025

(65) Prior Publication Data

US 2025/0241780 A1 Jul. 31, 2025

Related U.S. Application Data

(60) Provisional application No. 63/626,544, filed on Jan. 30, 2024.

(51) Int. Cl.

*A61F 5/03* (2006.01)
*A41C 3/00* (2006.01)
*A61F 13/14* (2006.01)

(52) U.S. Cl.

CPC .............. *A61F 5/03* (2013.01); *A41C 3/0064* (2013.01); *A61F 13/14* (2013.01)

(58) Field of Classification Search

CPC .. A61F 5/02; A61F 5/022; A61F 5/024; A61F 5/026; A61F 5/028; A61F 5/03; A61F 5/37; A61F 13/14; A61F 13/143; A61F 13/145; A61F 2007/0018; A61F 2007/0019; A61F 2007/0021; A41D 13/0518; A41D 13/1245; A41C 3/0064; A63B 21/065; A63B 21/4007; A45F 3/04; A45F 3/047;

(Continued)

(56) References Cited

U.S. PATENT DOCUMENTS 3,449,778 A * 6/1969 Jones ...................... B63C 9/115 441/112
6,379,208 B2 * 4/2002 Khanamirian .......... B63C 9/115 441/106

(Continued)

*Primary Examiner* — Keri J Nelson
(74) *Attorney, Agent, or Firm* — WPAT, PC

(57) ABSTRACT

A sternum stabilization vest includes two chest pads and a supporting structure. Each chest pad includes: a sponge; a cloth body covering the sponge; first and second front fixing straps arranged on front side of the cloth body with the later located above the former; and first and second front adjustment rings arranged on the first and second front fixing straps, respectively. The supporting structure includes: a back supporting cloth; side fixing straps arranged on both lateral sides of the back supporting cloth; side adjustment rings arranged at the side fixing straps; and side strap bodies arranged at both lateral sides of the back supporting cloth and located below the side fixing straps. The side strap bodies are threaded through the first front adjustment rings, the side adjustment rings and the second front adjustment rings in sequence, such that the extension paths of the side strap bodies form Z-shapes.

7 Claims, 17 Drawing Sheets

(58) Field of Classification Search
CPC ......... A45F 2003/045; A45F 2003/146; B63C 9/11; B63C 9/115; B63C 9/125; B63C 9/1255; A62B 35/0006
See application file for complete search history.

(56) References Cited

U.S. PATENT DOCUMENTS

| | | | | | |
|---|---|---|---|---|---|
| 6,503,215 | B1 * | 1/2003 | Reinhardt | A61F 5/028 | 602/41 |
| 6,773,318 | B1 * | 8/2004 | Albright | A41D 13/0125 | 441/118 |
| 9,681,692 | B2 * | 6/2017 | Hansen | A41C 3/0064 | |
| 9,854,851 | B2 * | 1/2018 | Blackwell | A61F 5/02 | |
| 9,949,863 | B2 * | 4/2018 | Leibowitz | A61F 5/03 | |
| 10,786,382 | B2 * | 9/2020 | Shagdar | A61B 5/1116 | |
| 10,932,504 | B1 * | 3/2021 | Gillam | A41D 13/0012 | |
| 11,517,482 | B2 * | 12/2022 | Lipshaw | A61F 13/146 | |
| 2008/0153370 | A1 * | 6/2008 | Wagner | B63C 9/11 | 441/115 |
| 2009/0131841 | A1 * | 5/2009 | Epple | A61F 5/30 | 602/19 |
| 2015/0032068 | A1 * | 1/2015 | Trane Jones | A61F 5/44 | 450/86 |
| 2021/0077290 | A1 * | 3/2021 | Van Beek | A61F 5/03 | |
| 2021/0346591 | A1 * | 11/2021 | Wyrick | A61M 1/985 | |
| 2022/0264971 | A1 * | 8/2022 | DeLara | A41D 13/1245 | |
| 2024/0350929 | A1 * | 10/2024 | Sparrow | A63H 3/003 | |

* cited by examiner

STERNUM STABILIZATION VEST

CROSS-REFERENCE TO RELATED APPLICATION

This application claims the priority of U.S. patent application No. 63/626,544, filed on Jan. 30, 2024, which is incorporated herewith by reference.

BACKGROUND OF THE INVENTION

1. Field of the Invention

The present invention relates to a sternum stabilization vest, particularly to a sternum stabilization vest that can be worn by a single individual.

2. The Prior Arts

Open-heart surgery refers to a surgery that involves opening the chest cavity to perform direct operations on the heart. During the open-heart surgery, the sternum usually needs to be sawed open to perform the surgery. After the surgery is completed, the sternum is reconnected with steel wires or other fixing materials, but is still requires time to fully heal. Therefore, the doctor typically recommends the patient to wear a sternum stabilization vest. The Sternum stabilization vest has the following functions: first, it limits excessive movement of the chest, stabilizes the sternum, and reduces the risk of sternal displacement caused by coughing, breathing, or movement; second, it provides appropriate pressurizing and support to alleviate post-operative pain and discomfort in chest, allowing patients to engage in daily activities with greater ease; third, it reduces the risk of sternal instability or separation, thereby lowering the likelihood of sternal infection or post-operative wound dehiscence in chest; fourth, when the patients cough, breath, or move, the sternum stabilization vest may provide support, such that the patients may safely perform necessary rehabilitation activities, for example, deep breathing exercises or light activities, which help prevent post-operative pulmonary complications such as pneumonia or atelectasis; five, it provides the patients with psychological sense of security, reducing their concerns about sternal displacement or the impact on the wound.

A known sternum stabilization vest comprises two chest pads and a supporting structure. Each chest pads comprises a sponge, a first cloth body, a second cloth body, a first front fixing strap, a second front fixing strap, a first front adjustment ring, a second front adjustment ring, an upper fixing strap, and an upper adjustment ring. The first cloth body covers the surface of the sponge with its front side provided with a hook side of a hook-and-loop fastener. The back side of the second cloth body is provided with a loop side of the hook-and-loop fastener, the hook side of the hook-and-loop fastener on the front side of the first cloth body is fixed at the loop side of the hook-and-loop fastener on the back side of the second cloth body. The front side of one of the second cloth bodies is provided with a male buckle and a hook side of a hook-and-loop fastener, and the front side of another one of the second cloth bodies is provided with a female buckle and a loop side of the hook-and-loop fastener. The male buckle on the front side of the one of the second cloth bodies is inserted into the female buckle on the front side of the another one of the second cloth bodies, and the hook side of the hook-and-loop fastener on the front side of the one of the second cloth bodies is fixed to the loop side of the hook-and-loop fastener on the front side of the another one of the second cloth bodies. The first front adjustment ring is arranged at the first front fixing strap and has a slot. The second front adjustment ring is arranged at the second front fixing strap and has a slot. The upper adjustment ring is arranged at the upper fixing strap and has a slot. The supporting structure comprises a back supporting cloth, four side strap bodies, and two upper strap bodies. Two of the side strap bodies are arranged at one lateral side of the back supporting cloth, another two of the side strap bodies are arranged at another lateral side of the back supporting cloth, each side strap body is provided with a hook side and a loop side of a hook-and-loop fastener. The upper strap bodies are arranged on the top of the back supporting cloth, each upper strap body is provided with a hook side and a loop side of a hook-and-loop fastener.

The following description explains how to assemble the chest pads and the supporting structure of a known sternum stabilization vest.

The side strap bodies are threaded through the side adjustment rings, and then the hook side of the hook-and-loop fastener of each side strap body is fixed to the loop side thereof. The upper strap bodies are threaded through the upper adjustment rings, and then the hook side of the hook-and-loop fastener of each upper strap body is fixed to the loop side thereof.

When the patient who has undergone an open-heart surgery wears the known sternum stabilization vest with it being not tightened, the chest pads are located at the front side of left and right chests of the patient, respectively, the back supporting cloth is located at the back of the patient, the side strap bodies pass both lateral sides of the patient's torso, respectively, and the upper strap bodies are located above the patient's shoulder.

However, the patient only has two hands, while there are four side strap bodies that extend laterally, making it impossible for the patient to grip and pull them outward on his/her own with just their two hands. Therefore, the patient usually needs two nursing staffs or two family members to stand on both sides, with four hands gripping the four side strap bodies to pull them outward at the same time, and then the chest pads and the back supporting cloth can be tightened.

Further, when the nursing staffs intend to change the wound dressing for the patient, they must separate the chest pads in several stages by separating the main and female buckles, and separating the hook and loop sides of the hook-and-loop fastener, which is quite cumbersome.

In addition, the shape of the sponges of the chest pads is rectangle, which does not correspond to the shape of the sternum, causing a poor effect for supporting the chest.

Besides, the material of the first cloth body of each chest pad does not have antibacterial effect, which causes the surface of the first cloth body to be prone to the growth of bacteria, fungi, and other microorganisms, which in turn increases the risk of odor, infection, or health issues caused by bacteria, fungi, and other microorganisms.

Moreover, the material supporting the cloth body is less breathable and cannot lower the surface temperature of skin, which makes it less comfort and results in the patient's low willingness to wear.

It is worth mentioning that a known sternum stabilization vest cannot be compatible with a wireless physiological monitoring device.

SUMMARY OF THE INVENTION

A main object of the present invention is to provide a sternum stabilization vest, in which the extension paths of side strap bodies are in Z-shapes, which is suitable for the patients to operate independently with both hands.

Another object of the present invention is to provide a sternum stabilization vest, in which two chest pads may be joined and separated by a zipper assembly.

Another object of the present invention is to provide a sternum stabilization vest, in which the shape of sponges of the chest pads corresponds to the shape of the sternum.

Another object of the present invention is to provide a sternum stabilization vest, in which a second substrate of a cloth body of the chest pads may effectively inhibit the growth of bacteria, fungi, and other microorganisms.

Another object of the present invention is to provide a sternum stabilization vest, in which a fourth substrate of a back supporting cloth provides a quite comfortable feel.

Another object of the present invention is to provide a sternum stabilization vest highly compatible with wireless physiological monitoring device.

In order to achieve the aforementioned objects, the present invention provides a sternum stabilization vest, comprising two chest pads and a supporting structure. Each chest pad includes a sponge, a cloth body, a first front fixing strap, a second front fixing strap, a first front adjustment ring, and a second front adjustment ring, wherein the cloth body covers a surface of the sponge, the first front fixing strap is arranged on a front side of the cloth body, the second front fixing strap is arranged on the front side of the cloth body and is located above the first front fixing strap, the first front adjustment ring is arranged at the first front fixing strap and has a slot, and the second front adjustment ring is arranged at the second front fixing strap and has two slots. The support structure includes a back supporting cloth, two side fixing straps, two side adjustment rings, and two side strap bodies, wherein the side fixing straps are arranged at both lateral sides of the back supporting cloth, respectively, the side adjustment rings are arranged at the side fixing straps, respectively, each of the side adjustment rings has a slot, and the side strap bodies are arranged at the both lateral sides of the back supporting cloth respectively and located below the side fixing straps. Wherein each corresponding side strap body is configured to be threaded through the slot of the first front adjustment ring, the slot of the side adjustment ring, and the slots of the second front adjustment ring in sequence, such that extension paths of the side strap bodies form Z-shapes.

In some embodiments, each chest pad further comprises an upper fixing strap and an upper adjustment ring, the upper fixing strap is arranged on top of the cloth body, the upper adjustment ring is arranged at the upper fixing strap and has a slot; the supporting structure further comprises two upper strap bodies arranged on top of the back supporting cloth, each upper strap body is provided with a hook side and a loop side of a hook-and-loop fastener; wherein each corresponding upper strap body is configured to be threaded through the slot of the upper adjustment ring, and then the hook side of the hook-and-loop fastener of corresponding upper strap body is fixed to the loop side thereof.

In some embodiments, the sternum stabilization vest further comprises a zipper assembly including a first zipper tape, a second zipper tape, a plurality of first zipper teeth, a plurality of second zipper teeth, a slider, a puller, a first stop, a second stop, a third stop, and an insertion pin, wherein the first zipper tape and the second zipper tape are arranged at one lateral side of the cloth body of corresponding chest pad, respectively, the first zipper teeth are arranged at one lateral side of the first zipper tape, the second zipper teeth are arranged at one lateral side of the second zipper tape, the slider is arranged at the one lateral side of the first zipper tape, the puller is arranged at the slider, the first stop is arranged at a top end of the first zipper tape, the second stop is arranged at a bottom end of the first zipper tape, the third stop is arranged at a top end of the second zipper tape, and the insertion pin is arranged at a bottom end of the second zipper tape; wherein after the insertion pin is inserted into the slider and the second stop, the slider is configured to be moved upward along the first zipper tape and the second zipper tape, such that the first zipper teeth mesh with the second zipper teeth.

In some embodiments, the sponge is trapezoidal in shape, and a length of the upper base of the sponge is longer than a length of the lower base thereof.

In some embodiments, the cloth body includes a first substrate and a second substrate, the first substrate covers top, bottom, a left side, a right side, and a front side of the sponge, the second substrate covers a back side of the sponge, and a material of the second substrate is antibacterial fabric.

In some embodiments, the supporting structure further includes two keeper rings each having a slot, wherein after being threaded through the slot of the side adjustment ring and before being threaded through one of the slots of the second front adjustment ring, the corresponding side strap body is configured to be threaded through the slot of the keeper ring for a first time; wherein after being threaded through another slot of the second front adjustment ring, the corresponding side strap body is configured to be threaded through the slot of the keeper rings for a second time.

In some embodiments, the back supporting cloth includes a third substrate and a fourth substrate, the third substrate is arranged on a back side of the back supporting cloth, the fourth substrate is arranged on a front side of the back supporting cloth, and a material of the fourth substrate is cooling fabric.

The effect of the present invention lies in that, since the extension paths of the side strap bodies are in Z-shapes, the patient who has undergone an open-heart may use both hands to grip the side strap bodies and pull them outward by himself/herself, and the chest pads and the back supporting cloth will be tightened, thereby the chest pads will firmly press against the left and right chests of the patient, and the back supporting cloth will firmly press against the back of the patient. This achieves the purpose of stabilizing the sternum, without the need for any assistance from the nursing staffs or family members.

Moreover, after the insertion pin is inserted into the slider and the second stop, the patient grips the puller to pull the slider upward along the first zipper tape and the second zipper tape, such that the first zipper teeth mesh with the second zipper teeth. When the chest wound of the patient who has undergone an open-heart surgery requires a dressing change, the patient only needs to grip the puller to pull the slider downward along the first zipper tape and the second zipper tape, such that the first zipper teeth are separated from the second zipper teeth until the insertion pin is detached from the slider and the second stop, then the zipper assembly can be unzipped, and the chest pads will be separated and no longer press against the chest. At this time, the nursing staff can change the wound dressing for the patient.

In addition, the shape of sponge corresponds to the shape of sternum, providing better effect for supporting the chest.

Moreover, the second substrate is closer to the chest, the second substrate made of antibacterial fabric may effectively inhibit the growth of bacteria, fungi, and other microorganism, reduce the density of bacteria and fungi, thereby reducing odor, infection or health issues caused by the bacteria, fungi and other microorganism.

Moreover, the fourth substrate is closer the back, the fourth substrate made of cooling fabric may lower the surface temperature of skin, improve comfort, and increase the patients' willingness to wear.

Furthermore, the sternum stabilization vest of the present invention is highly compatible with a wireless physiological monitoring device.

DETAILED DESCRIPTION OF THE PREFERRED EMBODIMENT

Figure 1:
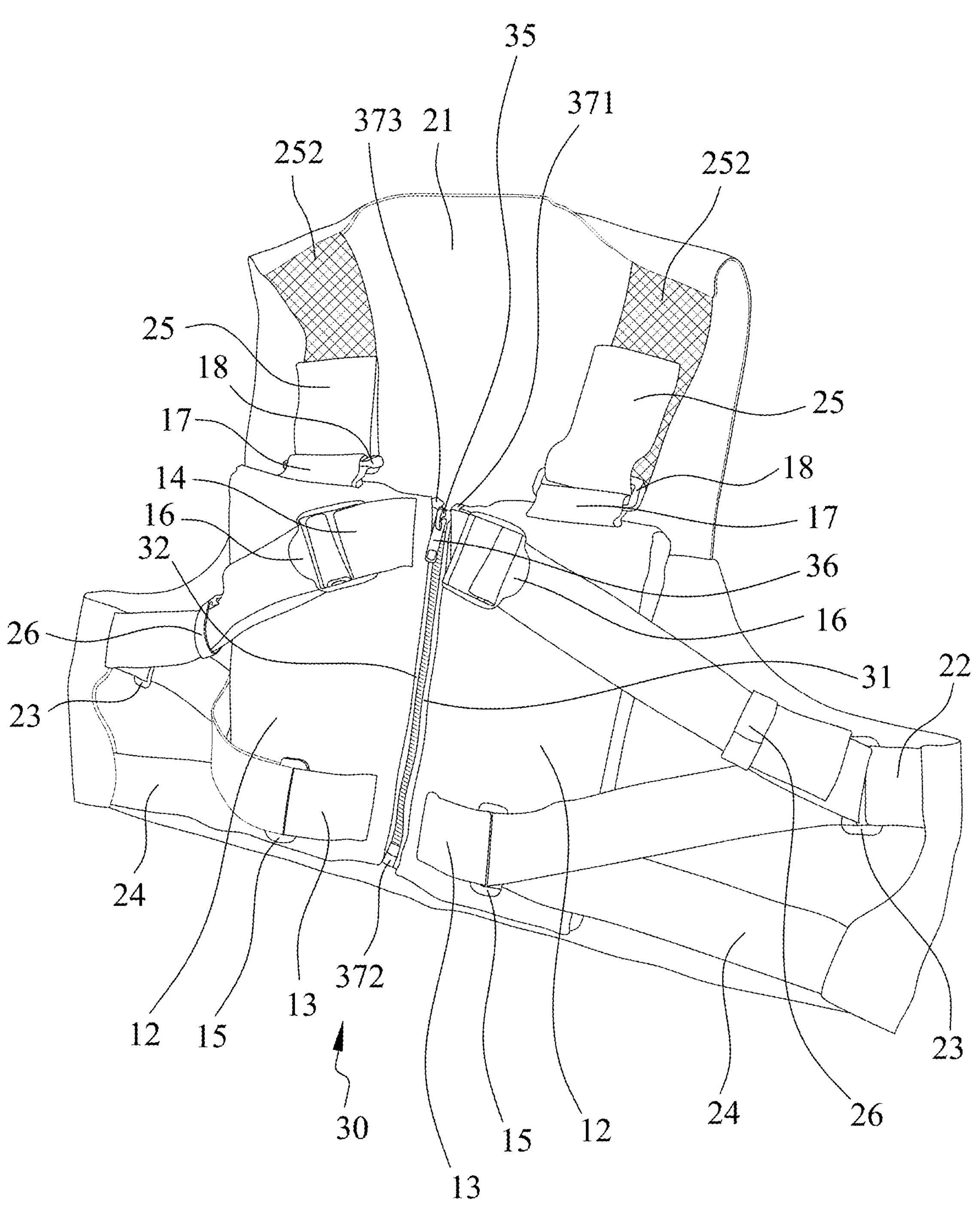
FIG. 1 is a perspective view of a sternum stabilization vest of the present invention.

The following provides a more detailed explanation of the embodiments of the present invention with reference to the drawings and reference numerals, such that those skilled in the art can implement it after reading this specification.

Figure 2:
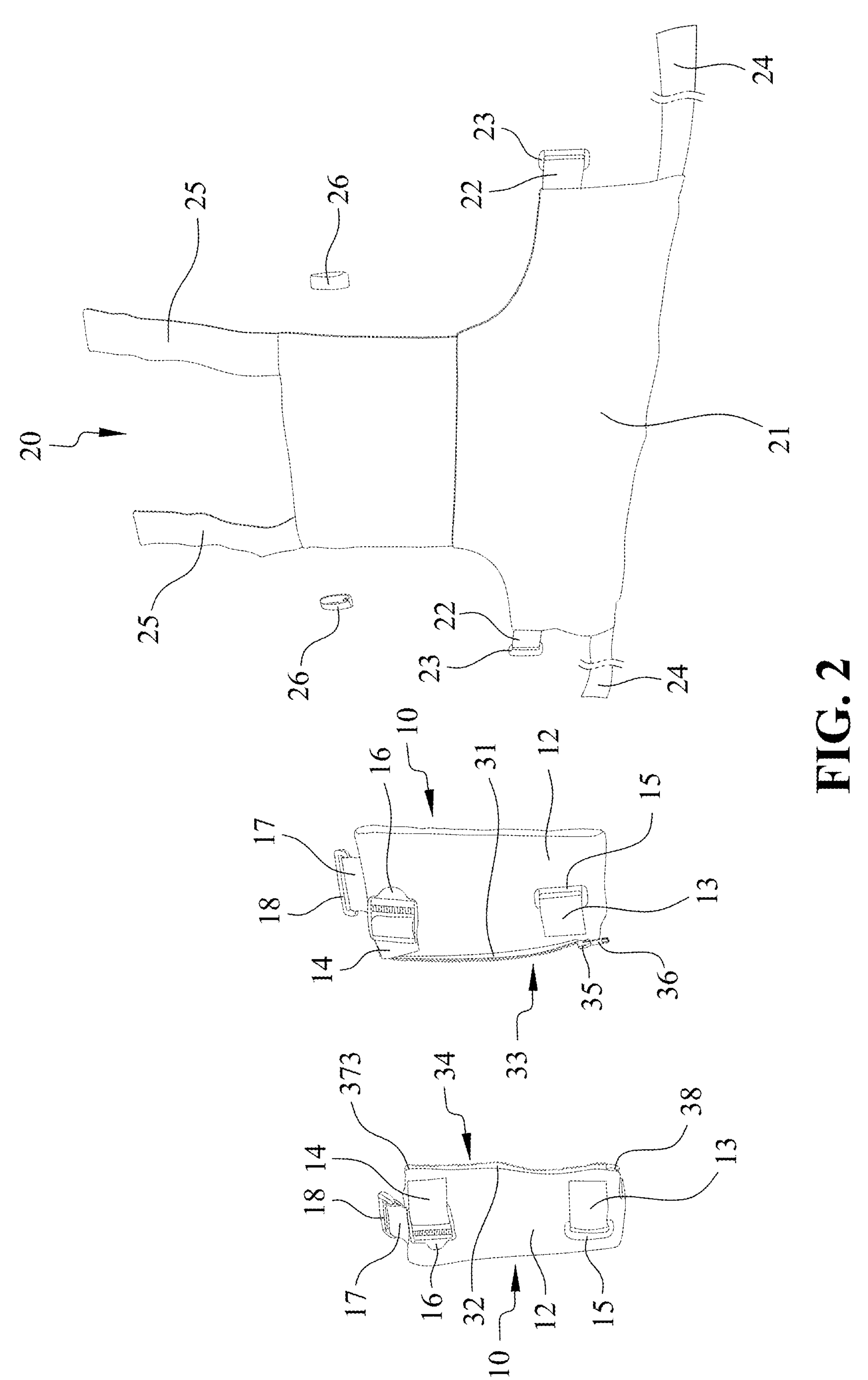
FIG. 2 is an exploded view of the sternum stabilization vest of the present invention.
Figure 3:
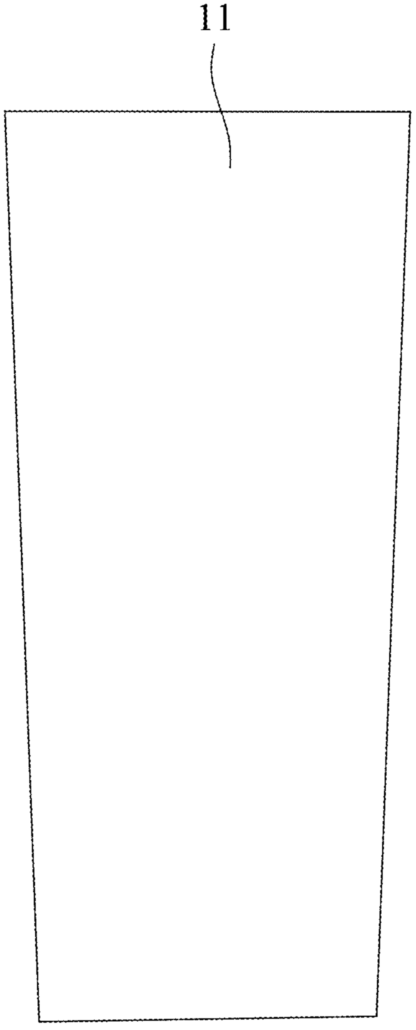
FIG. 3 is a schematic diagram of a sponge of the present invention.
Figure 4:
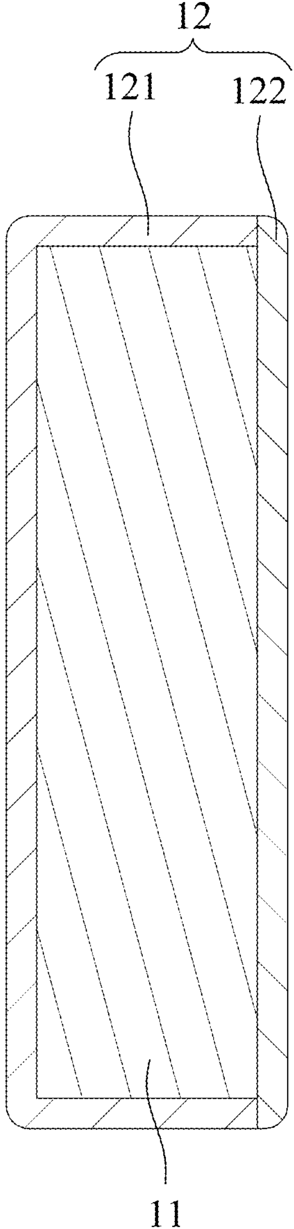
FIG. 4 is a cross-sectional view of a chest pad of the present invention.
Figure 5:
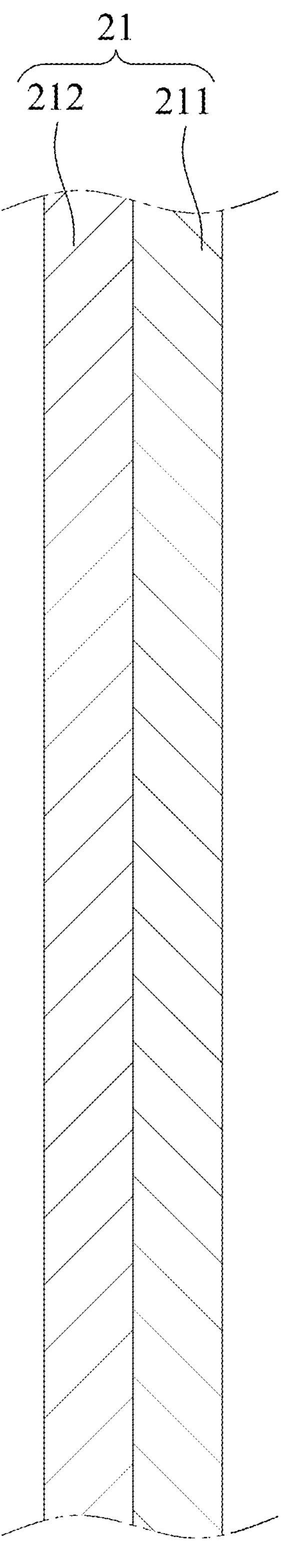
FIG. 5 is a cross-sectional view of a back supporting cloth of the present invention.

FIG. 1 is a perspective view of a sternum stabilization vest of the present invention. FIG. 2 is an exploded view of the sternum stabilization vest of the present invention. FIG. 3 is a schematic diagram of a sponge 11 of the present invention. FIG. 4 is a cross-sectional view of a chest pad 10 of the present invention. FIG. 5 is a cross-sectional view of a back supporting cloth 21 of the present invention. As shown in FIGS. 1 to 5, the present invention provides a sternum stabilization vest, which comprises two chest pads 10, a supporting structure 20, and a zipper assembly 30.

As shown in FIGS. 1 to 5, each chest pad 10 includes a sponge 11, a cloth body 12, a first front fixing strap 13, a second front fixing strap 14, a first front adjustment ring 15, a second front adjustment ring 16, an upper fixing strap 17, and an upper adjustment ring 18. The cloth body 12 covers the surface of the sponge 11. The first front fixing strap 13 is arranged on the front side of the cloth body 12. The second front fixing strap 14 is arranged on the front side of the cloth body 12 and is located above the first front fixing strap 13. The first front adjustment ring 15 is arranged at the first front fixing strap 13 and has a slot. The second front adjustment ring 16 is arranged at the second front fixing strap 14 and has two slots. The upper fixing strap 17 is arranged on the top of the cloth body 12. The upper adjustment ring 18 is arranged at the upper fixing strap 17 and has a slot.

As shown in FIGS. 1, 2, and 5, the supporting structure 20 includes a back supporting cloth 21, two side fixing straps 22, two side adjustment rings 23, two side strap bodies 24, two upper strap bodies 25, and two keeper rings 26. The side fixing straps 22 are arranged at both lateral sides of the back supporting cloth 21, respectively. The side adjustment rings 23 are arranged at the side fixing straps 22, respectively, and each of the side adjustment rings 23 has a slot. The side strap bodies 24 are arranged at both lateral sides of the back supporting cloth 21, respectively, and located below the side fixing straps 22. The upper strap bodies 25 are arranged on the top of the back supporting cloth 21, each upper strap body 25 is provided with a hook side 251 (shown in FIG. 12) and a loop side 252 of a hook-and-loop fastener. Each keeper ring 26 has a slot.

As shown in FIGS. 1 and 2, the zipper assembly 30 includes a first zipper tape 31, a second zipper tape 32, a plurality of first zipper teeth 33, a plurality of second zipper teeth 34, a slider 35, a puller 36, a first stop 371, a second stop 372, a third stop 373, and an insertion pin 38. The first zipper tape 31 and the second zipper tape 32 are arranged at one lateral side of the cloth body 12 of corresponding chest pad 10, respectively. The first zipper teeth 33 are arranged at one lateral side of the first zipper tape 31. The second zipper teeth 34 are arranged at one lateral side of the second zipper tape 32. The slider 35 is arranged at the one lateral side of the first zipper tape 31, and the puller 36 is arranged at the slider 35. The first stop 371 is arranged at the top end of the first zipper tape 31, and the second stop 372 is arranged at the bottom end of the first zipper tape 31. The third stop 373 is arranged at the top end of the second zipper tape 32, and the insertion pin 38 is arranged at the bottom end of the second zipper tape 32.

The following description explains how to assemble the chest pads 10 and the supporting structure 20 of the sternum stabilization vest of the present invention in combination with drawings.

Figure 6:
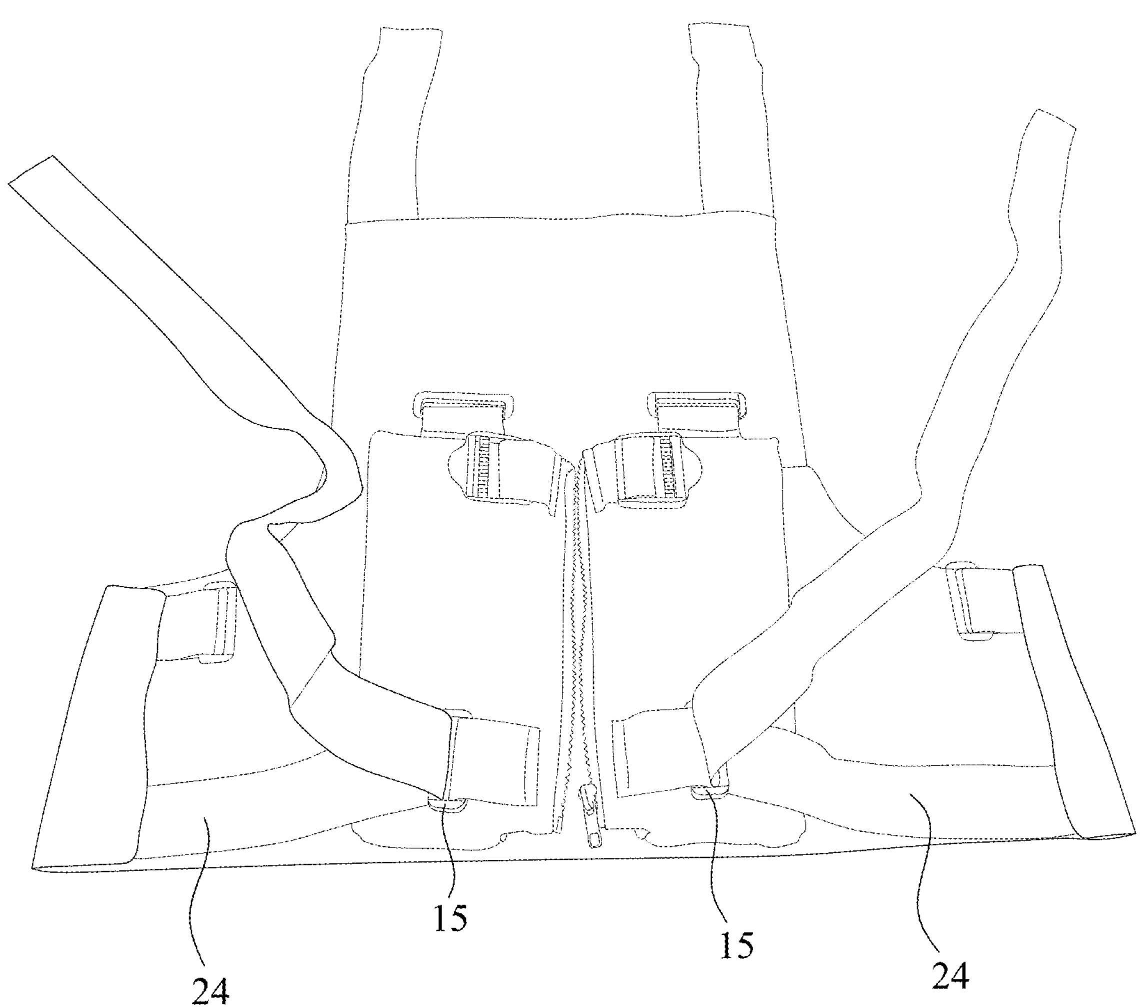
FIG. 6 is a schematic diagram showing that the side strap bodies are threaded through the first front adjustment rings in the present invention.
Figure 7:
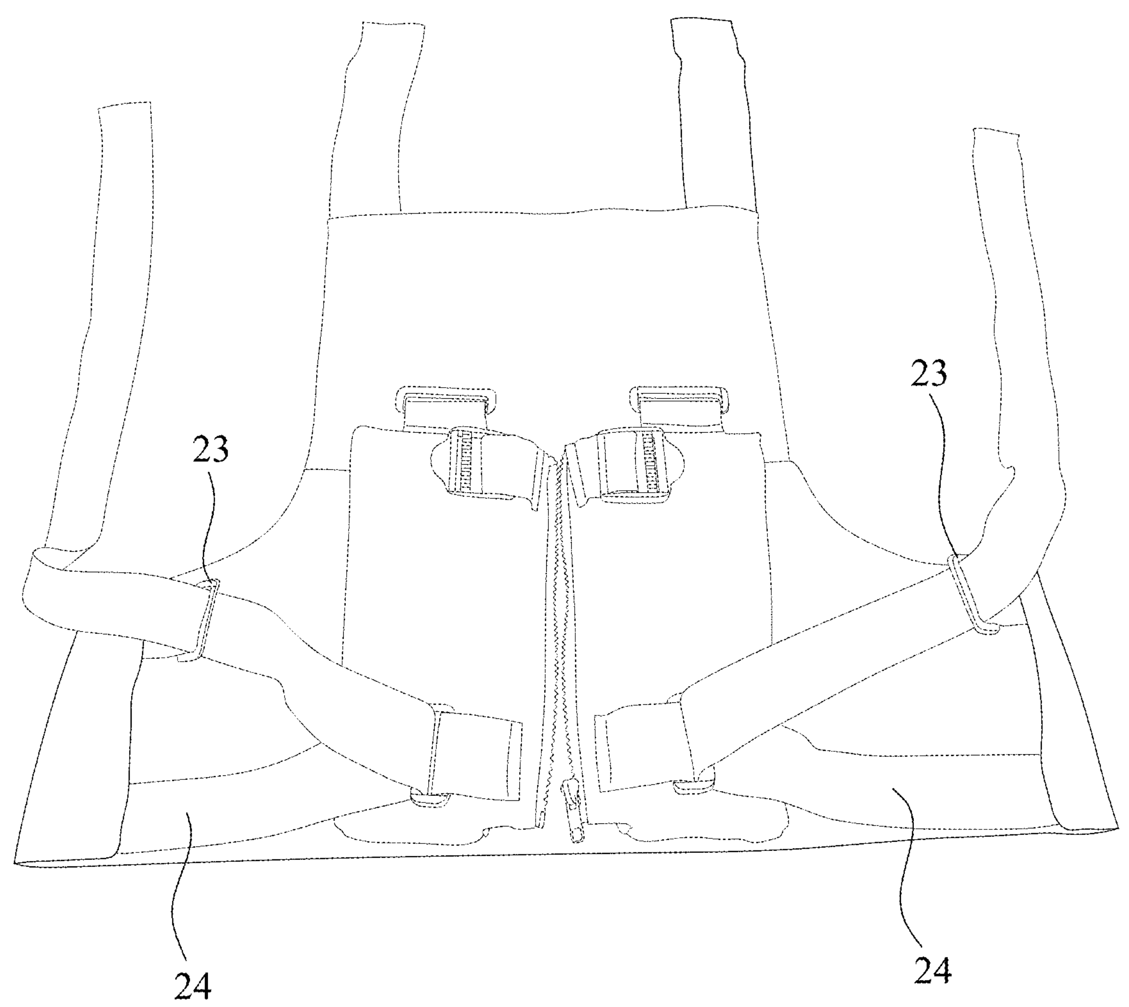
FIG. 7 is a schematic diagram showing that the side strap bodies are threaded through the side adjustment rings of the present invention.
Figure 8:
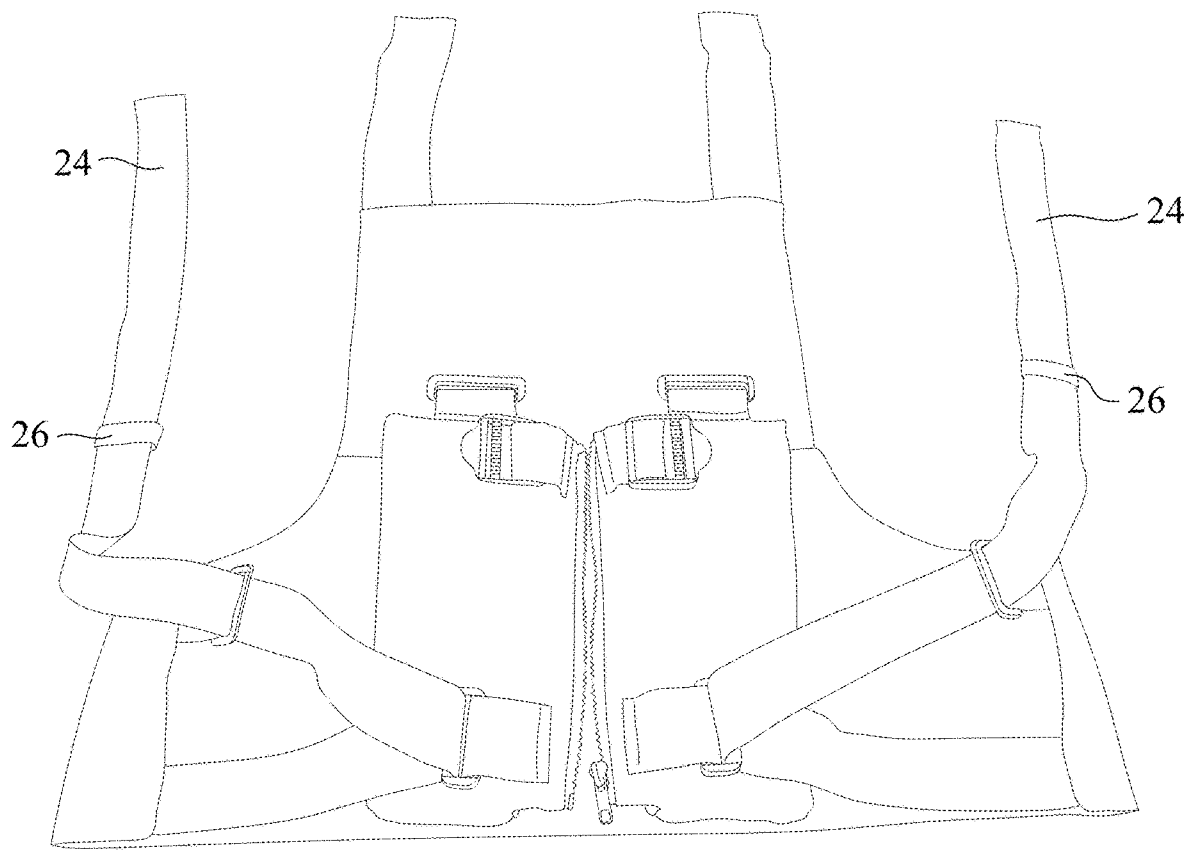
FIG. 8 is a schematic diagram showing that the side strap bodies are threaded through the keeper rings for a first time in the present invention.
Figure 9:
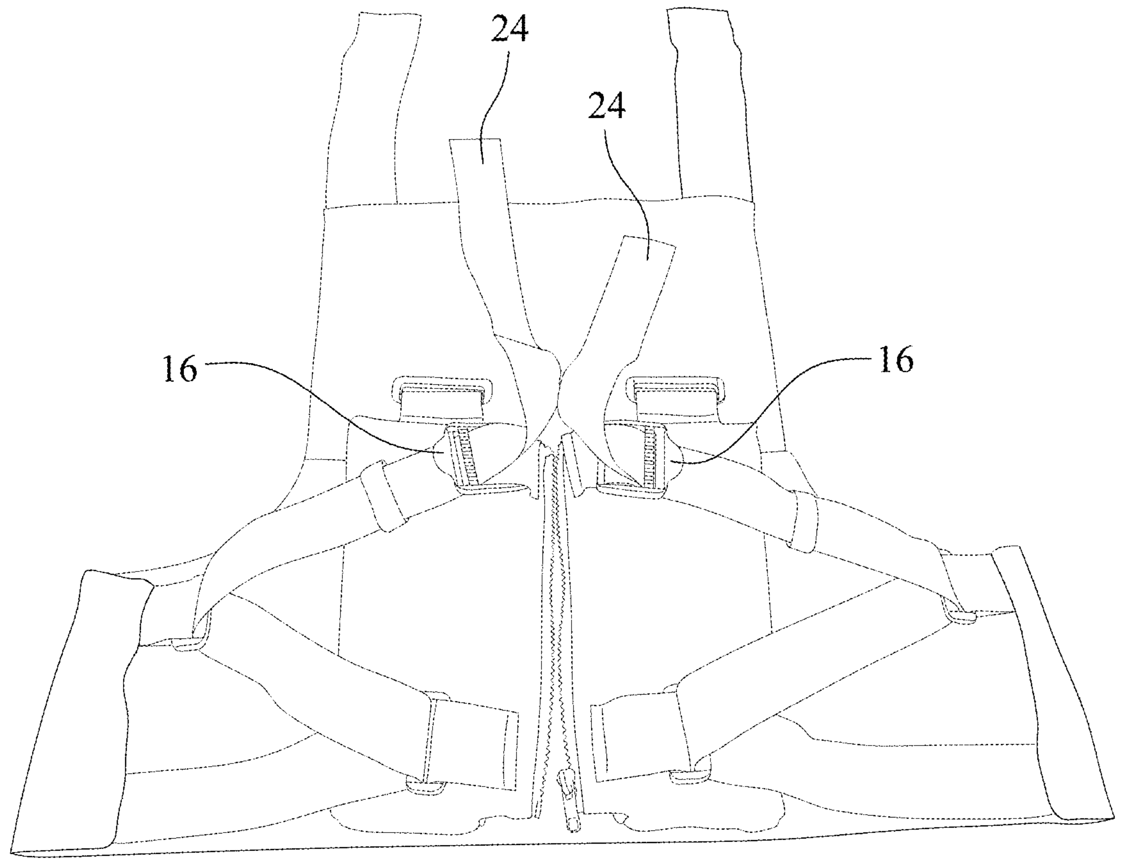
FIG. 9 is a schematic diagram showing that the side strap bodies are respectively threaded through one of the slots of corresponding second front adjustment ring in the present invention.
Figure 10:
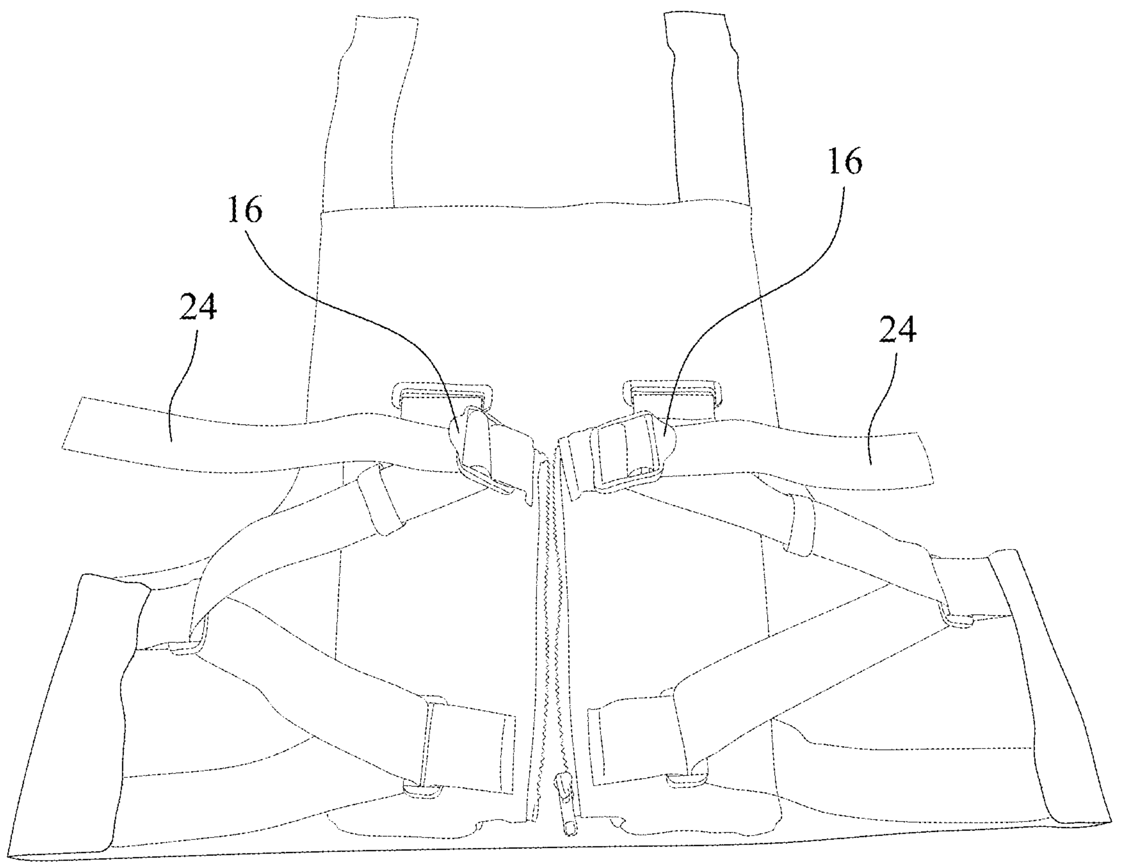
FIG. 10 is a schematic diagram showing that the side strap bodies are respectively threaded through the other slot of corresponding second front adjustment ring in the present invention.
Figure 11:
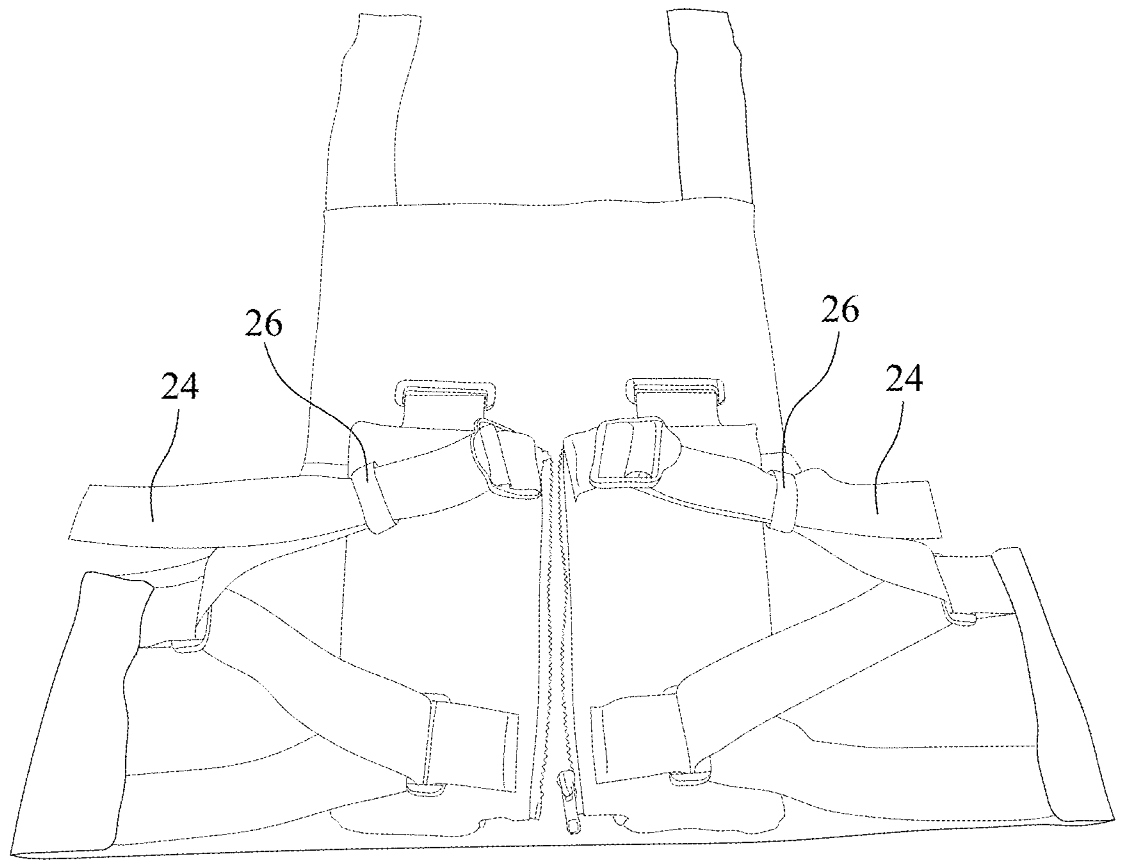
FIG. 11 is a schematic diagram showing that the side strap bodies are threaded through the keeper rings for a second time in the present invention.
Figure 12:
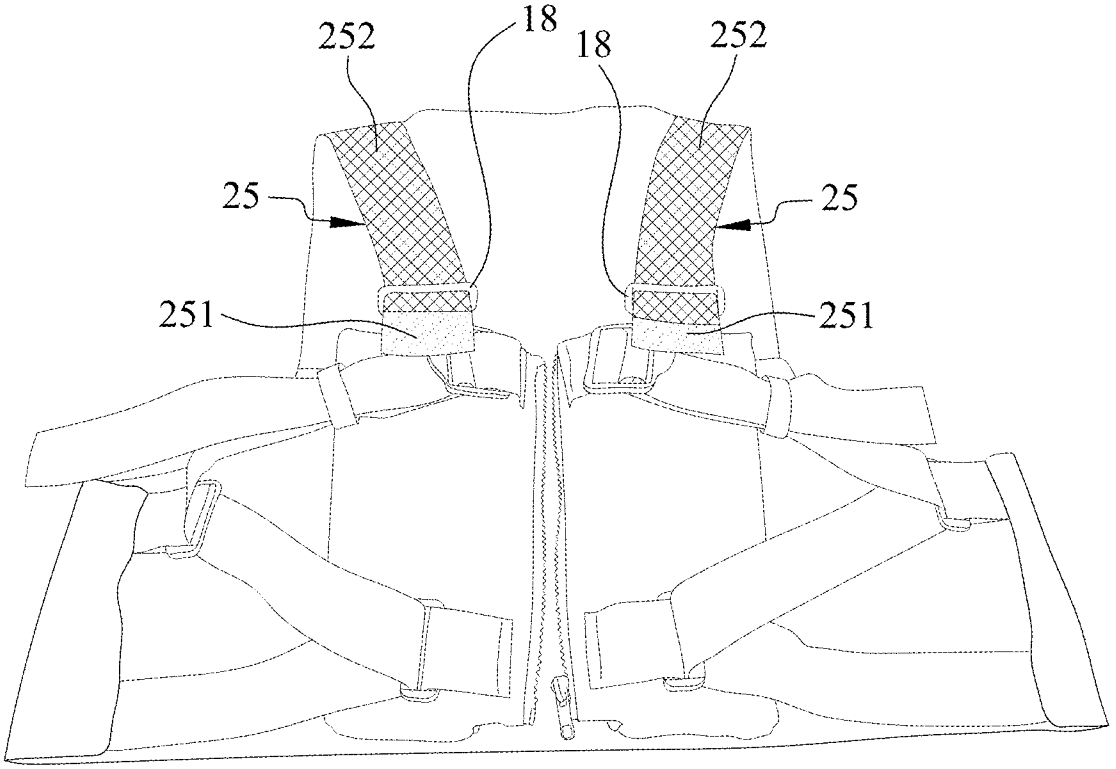
FIG. 12 is a schematic diagram showing that the upper strap bodies are threaded through the upper adjustment rings in the present invention.
Figure 13:
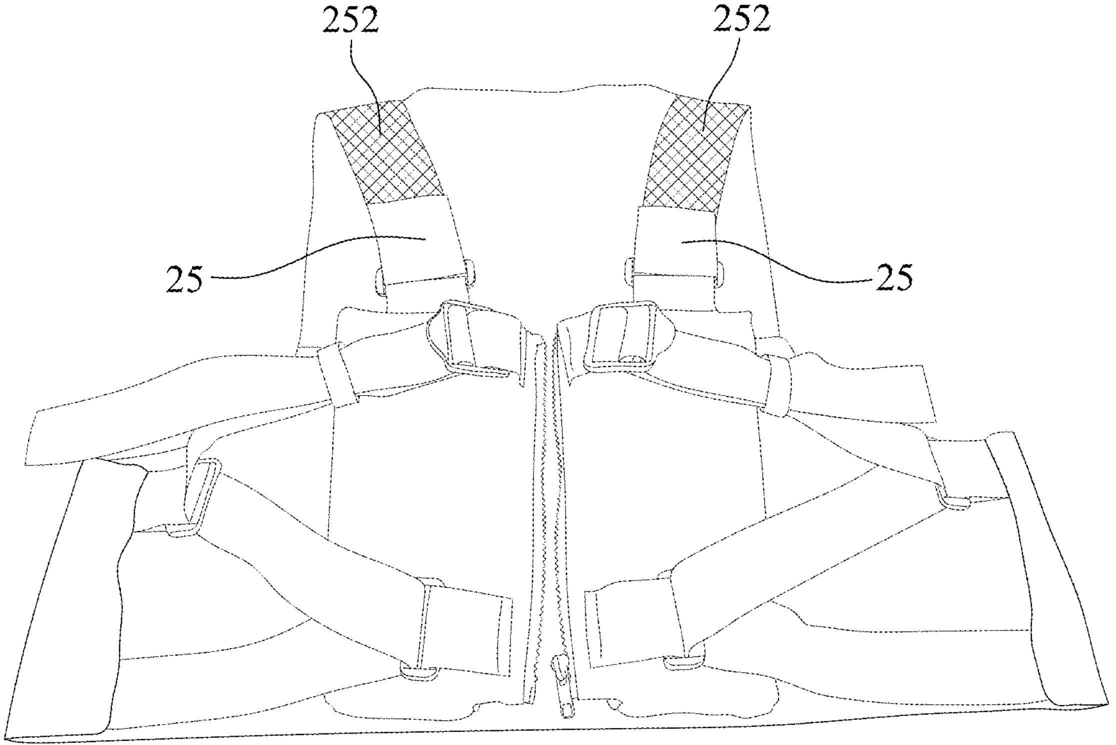
FIG. 13 is a schematic diagram showing that the hook side of a hook-and-loop fastener of the upper strap body is fixed to the loop side thereof in the present invention.
Figure 14:
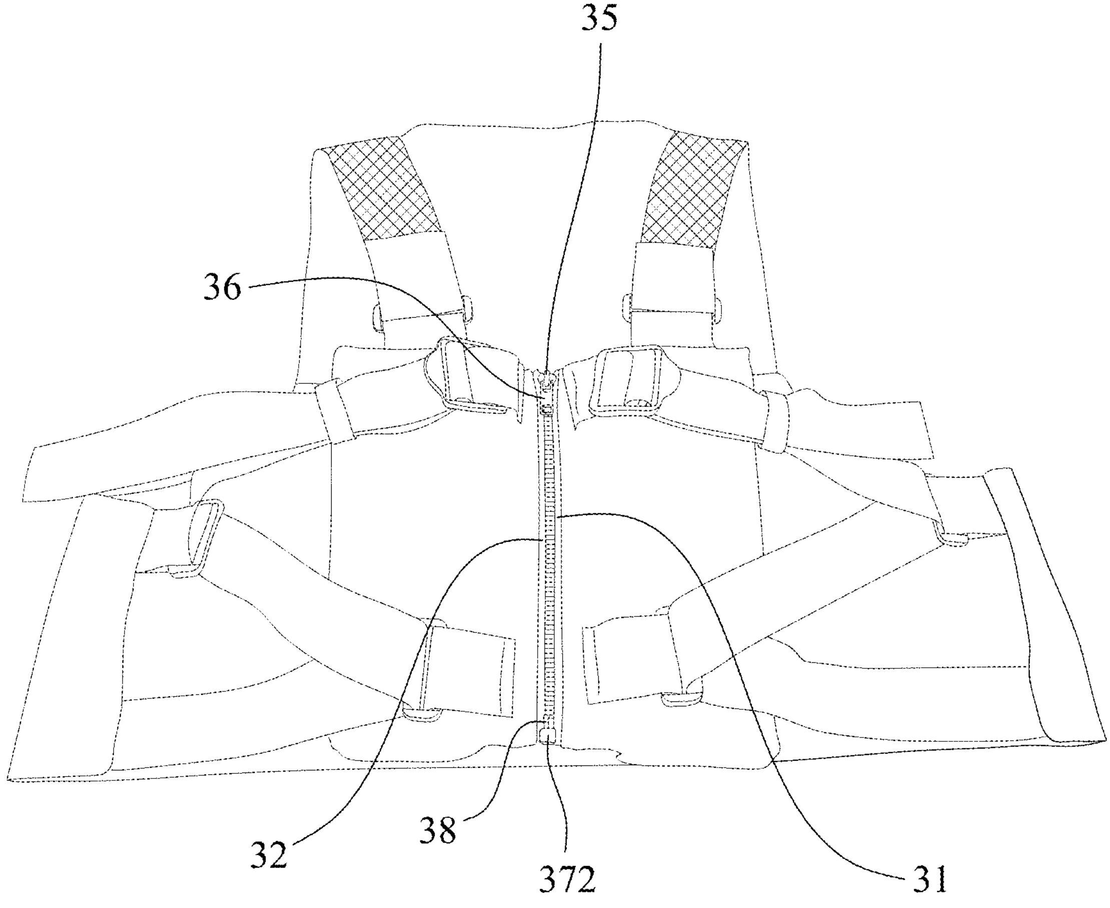
FIG. 14 is a schematic diagram showing that the zipper assembly fixes the chest pads in the present invention.

FIG. 6 is a schematic diagram showing that the side strap bodies 24 are threaded through the first front adjustment rings 15 in the present invention. FIG. 7 is a schematic diagram showing that the side strap bodies 24 are threaded through the side adjustment rings 23 in the present invention. FIG. 8 is a schematic diagram showing that the side strap bodies 24 are threaded through the keeper rings 26 for a first time in the present invention. FIG. 9 is a schematic diagram showing that the side strap bodies 24 are respectively threaded through one of the slots of corresponding second front adjustment ring 16 in the present invention. FIG. 10 is a schematic diagram showing that the side strap bodies 24 are respectively threaded through the other slot of corresponding second front adjustment ring 16 in the present invention. FIG. 11 is a schematic diagram showing that the side strap bodies 24 are threaded through the keeper rings 26 for a second time in the present invention. FIG. 12 is a schematic diagram showing that the upper strap bodies 25 are threaded through the upper adjustment rings 18 in the present invention. FIG. 13 is a schematic diagram showing that the hook side 251 of the hook-and-loop fastener of the upper strap body 25 is fixed to the loop side 252 thereof in the present invention. FIG. 14 is a schematic diagram showing that the zipper assembly 30 fixes the chest pads 10 in the present invention. As shown in FIGS. 6 to 11, each corresponding side strap body 24 is configured to be threaded through the slot of the first front adjustment ring 15, the slot of the side adjustment ring 23, one slot of the keeper ring 26, the slots of the second front adjustment ring 16, and another slot of the keeper ring 26 in sequence, such that the extension paths of the side strap bodies 24 form Z-shapes. As shown in FIGS. 12 and 13, each corresponding upper strap body 25 is configured to be threaded through the slot of the upper adjustment ring 18, and then the hook side 251 of the hook-and-loop fastener of corresponding upper strap body 25 is fixed to the loop side 252 thereof. As shown in FIG. 14, after the insertion pin 38 is inserted into the slider 35 and the second stop 372, the patient grips the puller 36 to pull the slider 35 upward along the first zipper tape 31 and the second zipper tape 32, such that the first zipper teeth 33 mesh with the second zipper teeth 34.

The chest pads 10 and the supporting structure 20 can be disassembled by the reverse action of those mentioned above.

Figure 15:
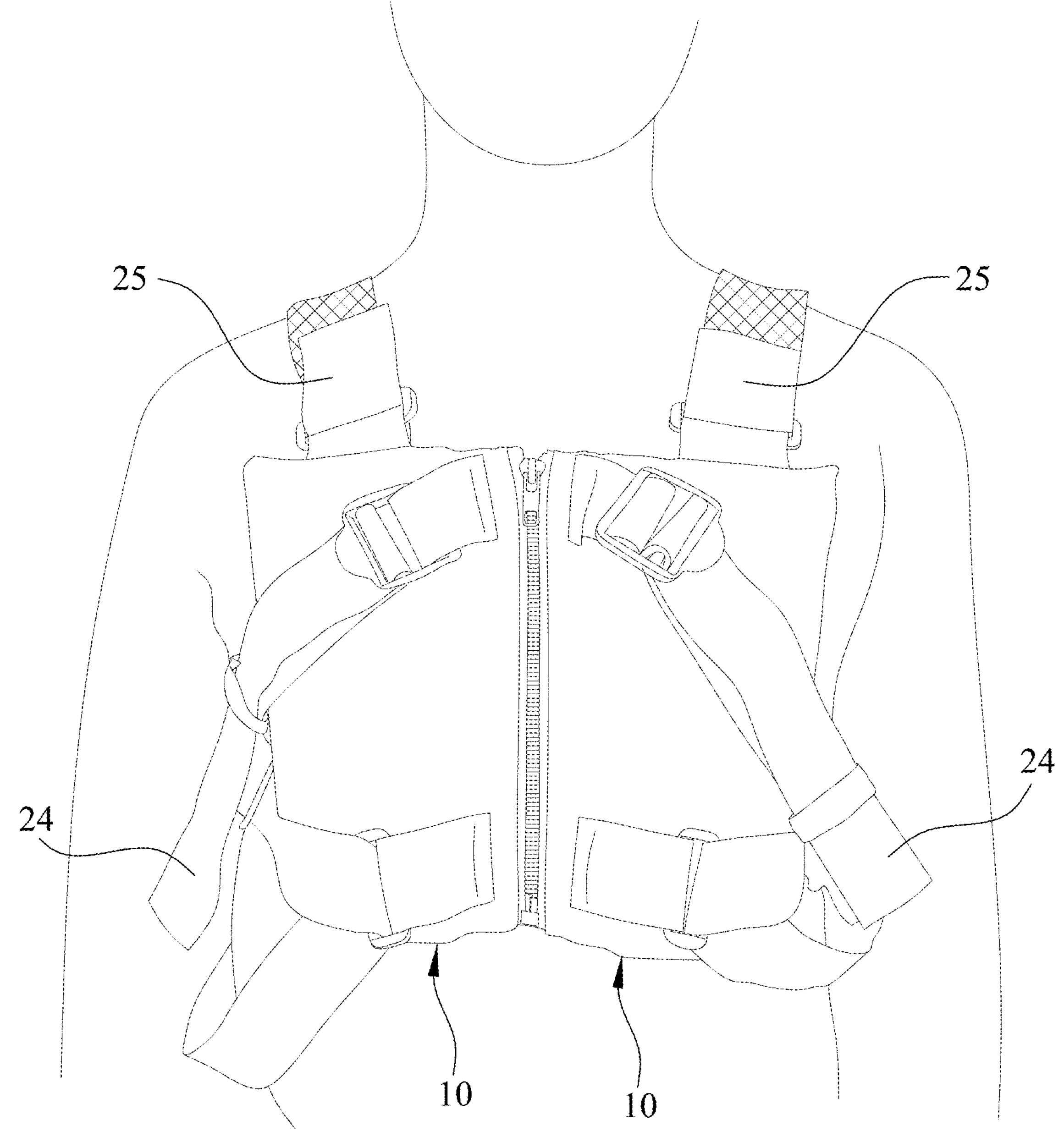
FIG. 15 is a schematic diagram showing that the patient who has undergone an open-heart surgery wears the sternum stabilization vest of the present invention and the side strap bodies have not been tightened.

FIG. 15 is a schematic diagram showing that the patient who has undergone an open-heart surgery wears the sternum stabilization vest of the present invention and the side strap bodies 24 have not been tightened. As shown in FIG. 15, when the patient who has undergone an open-heart surgery wears the sternum stabilization vest of the present invention and the side strap bodies 24 have not been tightened, the chest pads 10 are located at the front side of left and right chests of the patient, respectively, the back supporting cloth 21 is located at the back of patient, the side strap bodies 24 pass both lateral sides of the patient's torso, respectively, and the upper strap bodies 25 are located above the patient's shoulder.

Figure 16:
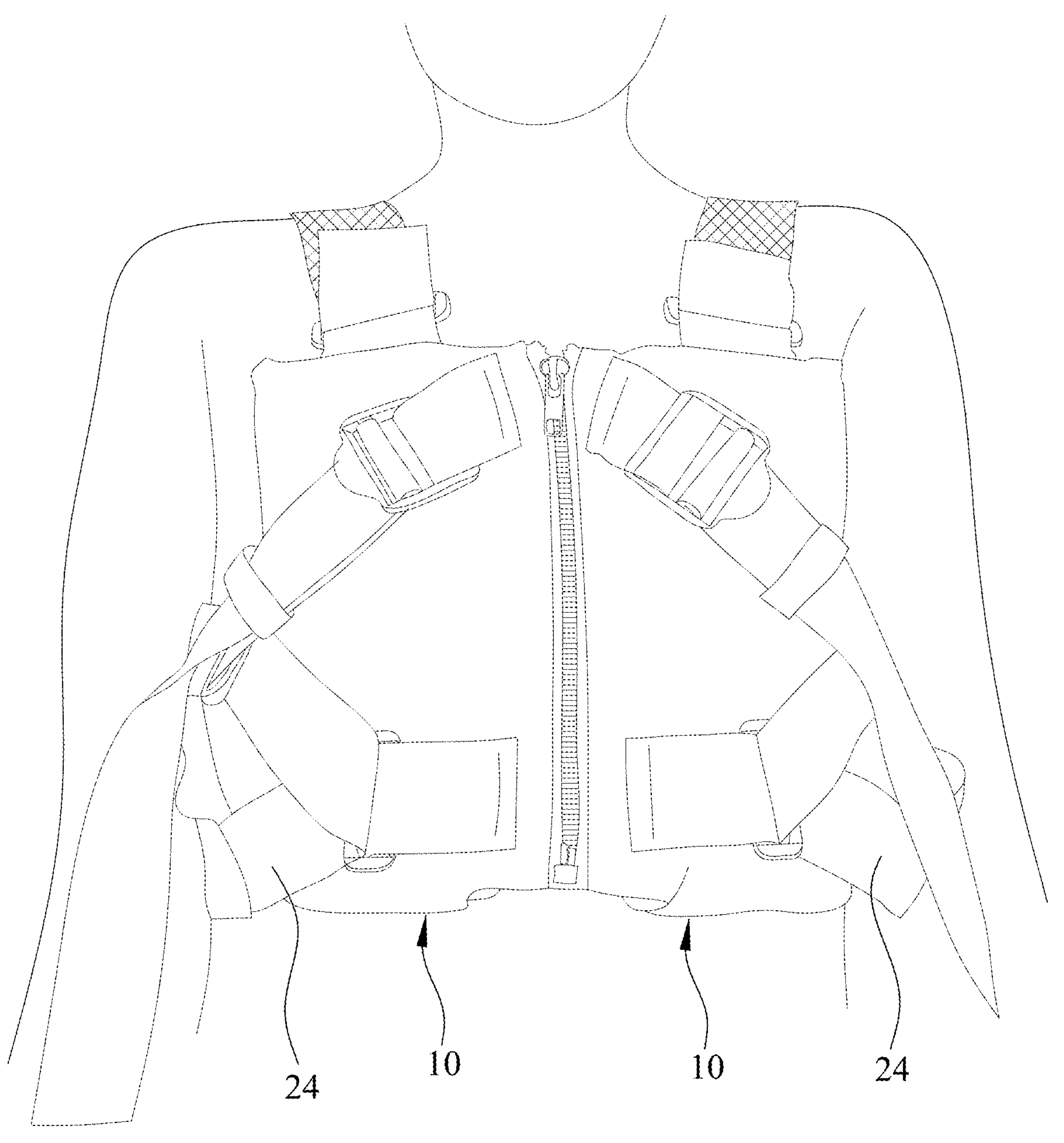
FIG. 16 is a schematic diagram showing that the sternum stabilization vest of the present invention is tightened.

FIG. 16 is a schematic diagram showing that the sternum stabilization vest of the present invention is tightened. As shown in FIG. 16, since the extension paths of the side strap bodies 24 are in Z-shapes, the patient who has undergone an open-heart may use both hands to grip the side strap bodies 24 and pull them outward by himself/herself, and the chest pads 10 and the back supporting cloth 21 will be tightened, thereby the chest pads 10 will firmly press against the left and right chests of the patient, and the back supporting cloth 21 will firmly press against the back of the patient. This achieves the purpose of stabilizing the sternum, without the need for any assistance from the nursing staffs or family members.

When the chest wound of the patient who has undergone an open-heart surgery requires a dressing change, the patient only needs to grip the puller 36 to pull the slider 35 downward along the first zipper tape 31 and the second zipper tape 32, such that the first zipper teeth 33 are separated from the second zipper teeth 34 until the insertion pin 38 is detached from the slider 35 and the second stop 372, then the zipper assembly 30 can be unzipped, and the chest pads 10 will be separated and no longer press against the chest. At this time, the nursing staff can change the wound dressing for the patient.

As shown in FIG. 3, in a preferred embodiment, the sponge 11 is trapezoidal in shape, and the length of the upper base of the sponge 11 is longer than the length of the lower base thereof. Therefore, the shape of the sponge corresponds to the shape of sternum, providing better effect for supporting the chest.

As shown in FIG. 4, in a preferred embodiment, the cloth body 12 includes a first substrate 121 and a second substrate 122. The first substrate 121 covers the top, bottom, left side, right side, and front side of the sponge 11, and the second substrate 122 covers the back side of the sponge 11. The material of the second substrate 122 is antibacterial fabric. In more detail, the second substrate 122 is closer to the chest, the second substrate 122 made of antibacterial fabric may effectively inhibit the growth of bacteria, fungi, and other microorganism, reduce the density of bacteria and fungi, thereby reducing odor, infection or health issues caused by bacteria, fungi and other microorganism.

As shown in FIG. 5, in a preferred embodiment, the back supporting cloth 21 includes a third substrate 211 and a fourth substrate 212. The third substrate 211 is arranged on the back side of the back supporting cloth 21, and the fourth substrate 212 is arranged on the front side of the back supporting cloth 21. The material of the fourth substrate 212 is cooling fabric. In more details, the fourth substrate 212 is closer to the back, the fourth substrate 212 made of cooling fabric may lower the surface temperature of skin, improve comfort, and increase the patients' willingness to wear.

Figure 17:
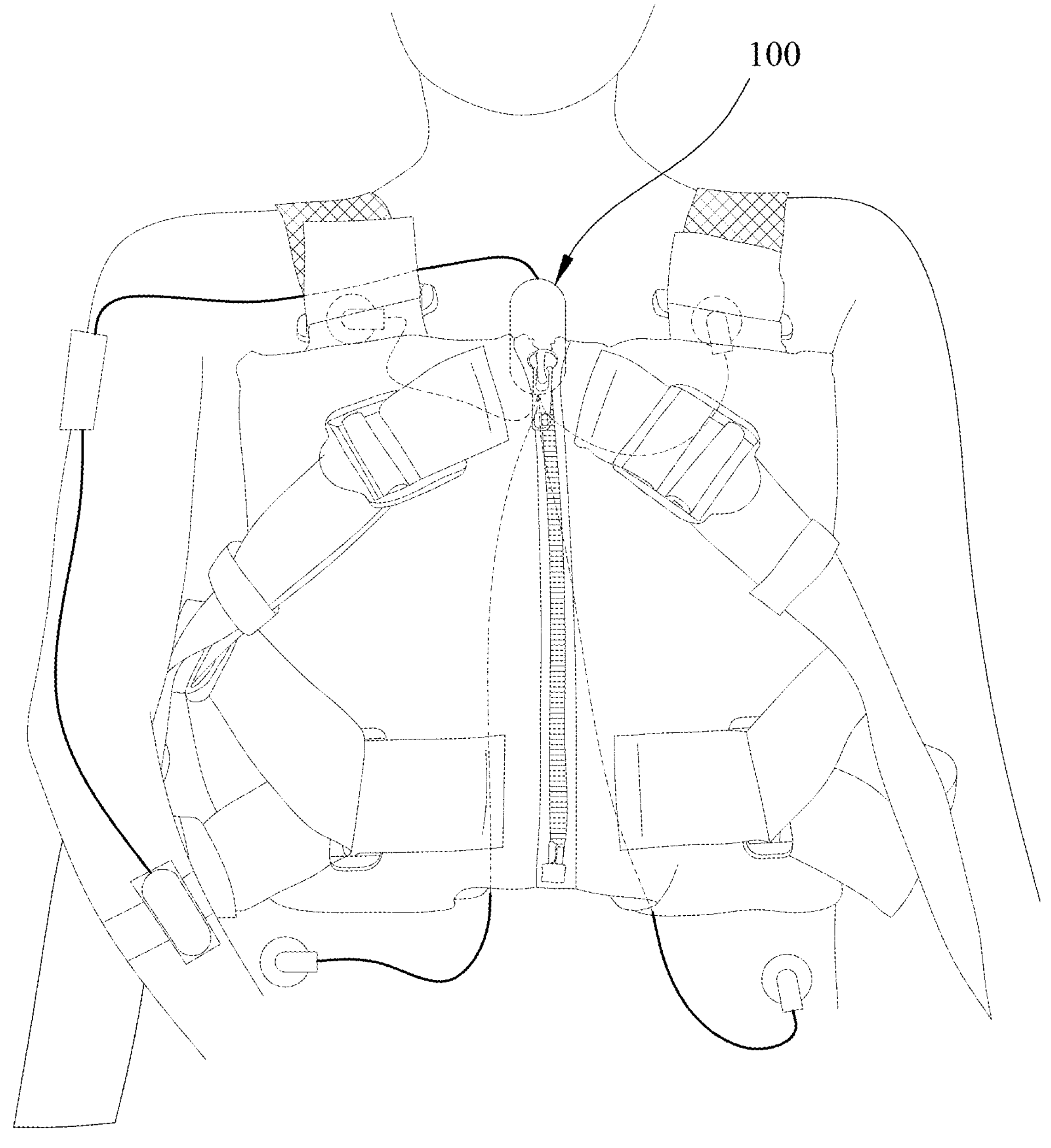
FIG. 17 is a schematic diagram showing that the patient who has undergone an open-heart surgery wears the sternum stabilization vest of the present invention and equipped himself/herself with a wireless physiological monitoring device.

FIG. 17 is a schematic diagram showing that the patient who has undergone an open-heart surgery wears the sternum stabilization vest of the present invention and equipped himself/herself with a wireless physiological monitoring device 100. As shown in FIG. 17, when the patient who has undergone an open-heart wears sternum stabilization vest of the present invention, he/she can also equip himself/herself with a wireless physiological monitoring device 100, and the sternum stabilization vest of the present invention is highly compatible with the wireless physiological monitoring device 100.

The aforementioned description is only intended to explain the preferred embodiments of the present invention, but not to impose any form of limitation on the present application. Therefore, any modifications or changes to the present invention made under the same inventive concept should still be included within the scope intended to be protected of the present application.

What is claimed is:

1. A sternum stabilization vest, comprising:

two chest pads, each including a sponge, a cloth body, a first front fixing strap, a second front fixing strap, a first front adjustment ring, and a second front adjustment ring, wherein the cloth body covers a surface of the sponge, the first front fixing strap is arranged on a front side of the cloth body, the second front fixing strap is arranged on the front side of the cloth body and is located above the first front fixing strap, the first front adjustment ring is arranged at the first front fixing strap and has a slot, and the second front adjustment ring is arranged at the second front fixing strap and has two slots; and a supporting structure, including a back supporting cloth, two side fixing straps, two side adjustment rings, and two side strap bodies, wherein the side fixing straps are arranged at both lateral sides of the back supporting cloth, respectively, the side adjustment rings are arranged at the side fixing straps, respectively, each of the side adjustment rings has a slot, and the side strap bodies are arranged at the both lateral sides of the back supporting cloth respectively and located below the side fixing straps;

wherein each corresponding side strap body is configured to be threaded through the slot of the first front adjustment ring, the slot of the side adjustment ring, and the slots of the second front adjustment ring in sequence, such that extension paths of the side strap bodies form Z-shapes.

2. The sternum stabilization vest of claim 1, wherein each chest pad further comprises an upper fixing strap and an upper adjustment ring, the upper fixing strap is arranged on top of the cloth body, the upper adjustment ring is arranged at the upper fixing strap and has a slot; the supporting structure further comprises two upper strap bodies arranged on top of the back supporting cloth, each upper strap body is provided with a hook side and a loop side of a hook-and-loop fastener;

wherein each corresponding upper strap body is configured to be threaded through the slot of the upper adjustment ring, and then the hook side of the hook-and-loop fastener of corresponding upper strap body is fixed to the loop side thereof.

3. The sternum stabilization vest of claim 1, further comprising: a zipper assembly including a first zipper tape, a second zipper tape, a plurality of first zipper teeth, a plurality of second zipper teeth, a slider, a puller, a first stop, a second stop, a third stop, and an insertion pin, wherein the first zipper tape and the second zipper tape are arranged at one lateral side of the cloth body of corresponding chest pad, respectively, the first zipper teeth are arranged at one lateral side of the first zipper tape, the second zipper teeth are arranged at one lateral side of the second zipper tape, the slider is arranged at the one lateral side of the first zipper tape, the puller is arranged at the slider, the first stop is arranged at a top end of the first zipper tape, the second stop is arranged at a bottom end of the first zipper tape, the third stop is arranged at a top end of the second zipper tape, and the insertion pin is arranged at a bottom end of the second zipper tape; wherein after the insertion pin is inserted into the slider and the second stop, the slider is configured to be moved upward along the first zipper tape and the second zipper tape, such that the first zipper teeth mesh with the second zipper teeth.

4. The sternum stabilization vest of claim 1, wherein the sponge is trapezoidal in shape, and a length of the upper base of the sponge is longer than a length of the lower base thereof.

5. The sternum stabilization vest of claim 1, wherein the cloth body includes a first substrate and a second substrate, the first substrate covers top, bottom, a left side, a right side, and a front side of the sponge, the second substrate covers a back side of the sponge, and a material of the second substrate is antibacterial fabric.

6. The sternum stabilization vest of claim 1, wherein the supporting structure further includes two keeper rings each having a slot, wherein after being threaded through the slot of the side adjustment ring and before being threaded through one of the slots of the second front adjustment ring, the corresponding side strap body is configured to be threaded through the slot of the keeper ring for a first time;

wherein after being threaded through another slot of the second front adjustment ring, the corresponding side strap body is configured to be threaded through the slot of the keeper rings for a second time.

7. The sternum stabilization vest of claim 1, wherein the back supporting cloth includes a third substrate and a fourth substrate, the third substrate is arranged on a back side of the back supporting cloth, the fourth substrate is arranged on a front side of the back supporting cloth, and a material of the fourth substrate is cooling fabric.

* * * * *